(12) United States Patent
Wallace

(10) Patent No.: US 6,949,582 B1
(45) Date of Patent: Sep. 27, 2005

(54) METHOD OF RELIEVING ANALGESIA AND REDUCING INFLAMATION USING A CANNABINOID DELIVERY TOPICAL LINIMENT

(76) Inventor: Walter H. Wallace, P.O. Box 5262, Katy, TX (US) 77491

( * ) Notice: Subject to any disclaimer, the term of this patent is extended or adjusted under 35 U.S.C. 154(b) by 216 days.

(21) Appl. No.: 10/243,059

(22) Filed: Sep. 13, 2002

Related U.S. Application Data

(63) Continuation of application No. 09/749,179, filed on Dec. 26, 2000, now abandoned, which is a continuation-in-part of application No. 09/321,178, filed on May 27, 1999, now abandoned.

(51) Int. Cl.$^7$ .................. A61K 31/35; A61K 31/05
(52) U.S. Cl. ............... 514/454; 514/456; 514/731; 514/733
(58) Field of Search .............. 514/454, 456, 514/731, 733

(56) References Cited

U.S. PATENT DOCUMENTS 4,464,378 A * 8/1984 Hussain ............. 514/282

OTHER PUBLICATIONS

Formukong et al, Inflammation, 12 (4), 1988, 361-371.*
Meng I et al, Nature, 395, 1998, 381-383.*
Richardson J et al, IASP Newsletter, 75, 1998m 111-119.*
Calignanao A et al,, Nature, 394, 1998, 277-281.*
Malfait A et al, Proceedings Natl. Acad. Sci., 9561, Aug. 2000.*
Touitou, E et al, International J. Pharmaceutics, 43, 1988, 9-15.*
Bond, J et al, J. Invest. Dermatol., Jun. 1988, 90 (6) 810-3.*
Morimoto, Y et al, J. Invest Dermatol., Aug. 1992, 44 (8), 634-9.*
Sato, K et al, J. Pharm. Sci., Feb. 1991, 80(2), 104-7.*
Griffin, G et al, J. Pharmacol. Exper. Ther., 292 (3), Mar. 2000, 886-894.*
Stanley-Cary, C et al, Behav. Pharmacol., Feb. 2002, 13(1), 15-28.*

* cited by examiner

*Primary Examiner*—Rebecca Cook
(74) *Attorney, Agent, or Firm*—Kenneth A. Roddy

(57) ABSTRACT

A method of relieving analgesia and reducing inflammation using a cannabinoid delivery topical liniment composition containing from about 97.5% to about 99.5% by weight a 70% monohydric alcohol solution, and from about 0.5% to about 2.5% by weight of a synergistic cannabinoid mixture extracted from the female plant *Cannabis sativa* L, including in combination: 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), terpenoids, and flavonoids. The liniment is applied topically, preferably by spraying, and the constituents of the mixture are absorbed through the skin and interact with cannabinoid receptors in the body and tissues of a human patient to produce therapeutic analgesic and anti-inflammatory effects without undesirable psychotropic side effects.

5 Claims, No Drawings

METHOD OF RELIEVING ANALGESIA AND REDUCING INFLAMATION USING A CANNABINOID DELIVERY TOPICAL LINIMENT

CROSS REFERENCE TO RELATED APPLICATION

This application is a Continuation-In-Part of U.S. patent application Ser. No. 09/749,179, filed Dec. 26, 2000, now abandoned, which is a Continuation-In-Part of U.S. patent application Ser. No. 09/321,178, filed May 27, 1999, now abandoned.

BACKGROUND OF THE INVENTION

1. Field of the Invention

This invention relates generally to topical analgesic and anti-inflammation agents and more particularly to the use of a rapid-onset cannabinoid delivery topical liniment for the relief of pain and reduction in inflammation associated with such ailments as arthritis, bursitis, fibromyalgia, carpal tunnel syndrome, gout, and other muscular and joint aches and pains, and to the medicinal topical liniment preparation containing cannabinoids.

2. Description of Related Art

Analgesia is the medical term for pain relief. Analgesia is typified by a reduction in inflammation or swelling, common physiological responses to injury. It is known that injured tissue sprouts new nerve fibers with even greater sensitivity to pain, a condition known as hyperalgia.

Cannabis sativa, commonly known as marijuana, and its major psychoactive ingredient, delta-9-tetrahydrocannabinol (THC), and various other cannabis constituents, termed cannabinoids, cannabinoids have been widely studied.

In an early study submitted for publication in 1987 and published in 1988, titled *"Transdermal Delivery of Tetrahydrocannabinol"* (Touitou et al, International Journal of Pharmaceutics, 43 (1988): 9–15), research was conducted to establish the route of drug penetration, to determine the permeation coefficient through rat and human skin in vitro (in a test tube), and to measure blood concentration time patterns in vivo (in a living organism) for formulations containing synthetic delta-8-THC with and without oleic acid, with the final goal being the design of a transdermal delivery system.

In another early study submitted for publication in 1991 and published in 1991, titled *"Localization of Molecules Penetrating Rat Skin In Vivo by Quantitative Autoradiography"* (Fabin et al, International Journal of Pharmaceutics, 74 (1991): 59–65), tests were conducted to investigate the localization and penetration pathways of two lipophilic compounds, tetrahydrocannabinol (THC) and oleic acid (OA) through the skin of live rats by means of a quantitative autoradiography technique, and a further goal was to learn the effect of carriers on the drug distribution between the rat skin layers and appendages of the two compounds. One test used pure Delta-8 THC in three different carriers: (1) a carrier of polyethylene glycol (PEG), (2) a carrier of Transcutol (diethylene glycol monoethyl ether), and (3) a carrier mixture of 7 parts propylene glycol (PG) and 3 parts ethanol (EtOH). The result of the investigation showed that after 2 hrs, the highest skin penetration of THC was observed from the Transcutol (diethylene glycol monoethyl ether) carrier but no significant difference was seen in the concentration of THC in the epidermis and in the appendages in all three systems. After 24 hours, the Transcutol system delivered the highest THC concentration to the various layers of the skin, and with the 7 parts propylene glycol (PG) and 3 parts ethanol (EtOH) carrier, the highest concentration of THC was in the epidermis and the lowest was lower in the dermis. It was also shown that a penetration enhancing agent, such as oleic acid (OH) may effect the localization of THC in the various skin layers. The highest concentration of drug was found in the epidermis and appendages.

Both of these studies utilized delta-8-THC rather than delta-9-THC or naturally occurring cannabinoids extracted from female cannabis green leaves of the plant *Cannabis sativa* L. Neither study discloses, with any specificity, the ratio of the THC component relative to the carrier component or the concentration per unit volume of the THC component. Neither study discloses or suggests any analgesic and anti-inflammatory properties of the THC formulation.

MARINOL® is a registered trademark of Unimed Pharmaceuticals, Inc., for a medicine, usually in soft gelatin capsule form, marketed by Roxane Laboratories, Inc., that contains the active ingredient "dronabinol" (a synthetic delta-9-THC solution) dissolved in sesame oil. The dronabinol content is usually 2.5, 5, or 10 mg. MARINOL® is not cannabis. It is single molecule THC and does not contain any of the other cannabinoids found in herbal cannabis.

Herbal cannabis obtained from the plant *Cannabis sativa*, contains more than 400 chemicals and approximately 60 cannabinoids, including: 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), and Cannabigerol (CBG). Cannabinoids are molecules unique to the cannabis plant, and are produced in epidermal glands on the leaves (especially the upper ones), stems, and the bracts that support the flowers. Herbal cannabis also includes more than a dozen terpenoids and several flavonoids.

After the 1988 Touitou et al and 1991 Fabin et al studies were published, there have been many very significant discoveries regarding the differences between single molecule synthetic THC and herbal cannabis, their biotransformation in the body, and interactions between THC and other cannabinoids and endogenous mechanisms in the body of mammals.

In August 1997, an Ad Hoc Group of Experts issued a report titled *"National Institute of Health—Workshop on the Medical Utility of Marijuana"*, at the request of the National Institutes of Health (NIH) following a meeting to review the scientific data concerning the potential therapeutic uses for marijuana and the need for and feasibility of additional research. The 1997 NIH report stated that the availability of THC in capsule form does not fully satisfy the need to evaluate the potential medical utility of marijuana. The Expert Group noted that, although delta-9-tetrahydrocannabinol is the principal psychoactive component of the cannabis leaf, there may be other compounds in the in the leaf that have useful therapeutic properties. Furthermore, the bioavailability and pharmacokinetics of THC from smoked marijuana are substantially different than those of the oral dosage form.

In January, 1997, the White House Office of National Drug Control Policy (ONDCP) requested the Institute of Medicine (IOM) to conduct a review of the scientific evidence for assessing the potential health benefits and risks of marijuana and its constituent cannabinoids. The pharmacology of marijuana and its major psychoactive ingredient, delta-9-tetrahydrocannabinol (THC) were reviewed, and the evidence for claims of therapeutic benefits was evaluated and presented in a report, titled *"Marijuana and Medicine: Assessing the Science Base"* (Institute of Medicine, March 1999).

On page 34 of the IOM report, Table 2.1 shows that the first conclusive evidence of specific cannabinoid receptors was discovered in 1988 and the cannabinoid brain receptor (CB1) was cloned, its DNA identified, and its location in the brain was discovered in 1988 (after the date Touitou et al study was submitted for publication). The cannabinoid receptor (CB2) that is outside the brain but is related to the brain receptor (CB1) was discovered in 1993 (after the publication date of both the Touitou et al study and the Fabin et al study).

"Cannabinoid receptors" are cells in the brain and other organs that contain specific protein receptors which recognize THC and some other cannabinoids and trigger cell responses. Other cannabinoids do not bind to these cannabinoid receptors and exert their effects by other ways. CB1 receptors are found in high concentrations within the brain and spinal cord. They are also present in certain peripheral cells and tissues (some neurons, some endocrine glands, leukocytes, spleen, heart and parts of the reproductive, urinary and gastrointestinal tracts). CB2 receptors are expressed primarily by immune cells und tissues (leukocytes, spleen and tonsils).

The discovery of specific cannabinoid receptors prompted the search for putative naturally occurring chemicals, known as "endocannabinoids", that interact with the receptors. "Endocannabinoids" or "endogenous cannabinoids" are naturally occurring compounds produced by the body of humans and animals that bind to the same receptors as cannabis. The most important are "anandamide" (arachidonyl-ethanolamide, "2-AG" (2-arachidonyl glycerol), and "PEA" (palmitylethanolamide). The endocanabinoid "anandamide" was discovered in 1992 (after the publication date of both the Touitou et al study and the Fabin et al study). Anandamide binds to CB1 cannabinoid receptors, and its activity parallels, to a large extent, that of delta-9-THC, the active constituent of Cannabis.

Endogenous cannabinoids (endocannabinoids) are a class of lipid-like molecules that share receptor binding sites with plant-derived cannabinoids and mimic many of their neurobehavioral effects (Mechoulam et al. *Adv. Exp. Bio. Med.* 1996, 402: 95–101.)

Cannabinoid receptor "agonists" are compounds that activate receptors. Binding to a receptor triggers an event or series of events in the cell that results in the cell's activity, its gene regulation or the signals it sends to neighboring cells. Receptor "antagonists" selectively bind to a receptor that would have been otherwise been available for binding to some other compound or drug. Antagonists block the effects of agonists and are tools to identify the functions of a receptor by showing what happens when its normal functions are blocked. Agonists and antagonists are both "ligands"; that is, they bind to receptors. The first specific cannabinoid antagonist SR141716A was developed in 1994 and the first cannabinoid antagonist SR144528 that can distinguish between CB1 and CB2 receptors was discovered in 1998 (after the publication date of both the Touitou et al study and the Fabin et al study).

Authors of the 1999 IOM report cite clinical data on effects of cannabinoids on chronic pain from studies of cancer pain, conducted by Noyes et al. Cancer pain can be due to inflammation, mechanical invasion of bone or other pain-sensitive structure, or nerve injury. It is severe, persistent, and often resistant to treatment with opioids. In one double blind controlled cross over study, Noyes and coworkers found that delta-9-tetrahydrocannabinol had analgesic effects equivalent to codeine (R. Noyes et al., *"The analgesic properties of delta-9- tetrahydrocannabinol and codeine,"* Clinical Pharmacology and Therapeutics 18 (1975): 84–89). A second study by Noyes et al determined that THC produced significant analgesia, anti-emesis, and enhanced appetite in patients with cancer pain (R. Noyes et al., *"Analgesic effect of delta-9-tertahydrocannabinol,"* Journal of Clinical Pharmacology 15 (1975): 139–143). After reviewing this and other clinical data, IOM researchers concluded that cannabinoids reduce painful stimuli to an extent comparable to opiates in potency and efficacy, and that the available evidence from animal and human studies indicate that cannabinoids can have a substantial analgesic effect.

Recent research further demonstrates that cannabis, cannabinoids and endocannabinoids function as analgesic and anti-inflammatory agents. In a report dated Jun. 11, 2001, titled *"Canadian Consortium for the Investigation of Cannabinoids in Human Therapeutics(CCIC)"*, evidence is presented regarding the interaction of cannabinoids on specific cannabinoid receptors to produce analgesic and anti-inflammation effects. On page 5, section 1.5, the report summarizes that the evidence supports that cannabinoids are analgesic, that an endocannabinoid system is a part of the bodies pain defense network and that the analgesic effect occurs at multiple levels from the brain to the peripheral nerve (pg 5, section 1.5). The report indicates that in addition to direct analgesic effects there is evidence that cannabinoids are anti-inflammatory (pg. 8, section 1.6). Cannabinoids act on CB2 receptors located on mast cells (cells involved in the bodies infection and injury defense system) to directly attenuate the release of inflammatory agents such as histamine and serotonin (Facci 1995). Palmitoylethanolamide (PEA), a CB2 agonist attenuates carageenan-induced mechanical hyperalgesia and edema by down-modulating mast cell formation after injury (Mazzari 1996). The dimethylheptyl derivative of THC-11 oic acid, a non-psychoactive derivative, supresses acute and chronic inflammatory changes in mice when given orally (Zurier 1998). Another non-psychoactive cannabinoid, HU-211, has been shown to supress inflammation that is caused by mobilization of cytokines such as TNFα (Bass 1996, Shohami 1997). Thus there is evidence that cannabinoids can exert a number of anti-inflammatory effects with significant potential applications in the treatment arthritis.

A 1998 rat study explained that THC taps circuitry at the base of the brain, modulating pain signals in a fashion similar to morphine and other opiates (I. Meng et al. *"An analgesic circuit activated by cannabinoids."* Nature 395 (1998): 381–383). Lead researcher Dr. Ian Meng determined that the results show that analgesia produced by cannabinoids and opioids involves similar brain stem circuitry and that cannabinoids are indeed centrally acting analgesics with a new mechanism of action.

The development of the CB1 cannabinoid antagonist SR141716A in 1994 and the more recent cannabinoid antagonist SR144528 in 1998, that can distinguish between CB1 and CB2 receptors, provided direct evidence of the existence of functional endogenous agonists for the two receptors, and permitted a much greater level of certainty in the interpretation of pharmacological data. It has been well established that endocannabinoids (the naturally occurring compounds that bind to the same receptors as cannabis) act primarily via the CB1 receptor to produce significant analgesia in the central nervous system (CNS). However, the effects of endocannabinoids acting on receptors in the periphery (outside the central nervous system) were until recently unknown.

In a 1998 study researchers demonstrated that cannabinoids produce anti-hyperalgesia via interaction with a peripheral CB1 receptor. (J. D. Richardson et al, *"Cannabinoids reduce hyperalgesia and inflammation via interaction with peripheral CB1receptors."* IASP Newsletter (International Association for the Study of Pain) 75 (1998): 111–119). Peripheral, but not systemic, administration of 0.01 ng of the endocannabinoid anandamide inhibited the induction of hyperalgesia. Peripheral administration of anandamide also attenuated hyperalgesia after its development via interaction with the CB1 cannabinoid receptor subtype as indicated by its reversal with the CB1 receptor antagonist SR 141716A. Additionally, peripheral, but not systemic, administration of 0.01 ng anandamide inhibited edema. Peripherally administered cannabinoids also interacted with CB1 receptors to inhibit capsaicin-evoked plasma extravasation into the hindpaw of rats. The researchers hypothesized that one potential mechanism for the anti-inflammatory actions of the cannabinoids is the inhibition of neurosecretion from the peripheral terminals of nociceptive primary afferent fibers. This hypothesis was supported by the finding that anandamide inhibited capsaicin-evoked release of calcitonin gene-related peptide from isolated hindpaw skin. Collectively, these results indicate that cannabinoids reduce inflammation via interaction with a peripheral CB1 receptor. A potential mechanism for this effect is the inhibition of neurosecretion from capsaicin-sensitive primary afferent fibers.

Recent research indicates that some endocannabinoids attenuate pain produced by chemical damage to cutaneous tissue by interacting with CB1 cannabinoid receptors located outside the central nervous system (CNS), and that they can also act "synergistically" by activating peripheral CB2 receptors.

In 1998, scientists at the University of Naples in Italy demonstrated that the endocannabinoid anandamide attenuates the pain behavior produced by chemical damage to cutaneous tissue by interacting with CB1-like cannabinoid receptors located outside the central nervous system (CNS). The endocannabinoid Palmitylethanolamide (PEA), which is released together with anandamide from a common phospholipid precursor, exerts a similar effect by activating peripheral CB2-like receptors. The report states: "When administered together, the two compounds act synergistically, reducing pain responses 100-fold more potently than does each compound alone." Gas-chromatography/mass-spectrometry measurements indicate that the levels of anandamide and PEA in the skin are enough to cause a tonic activation of local cannabinoid receptors. In agreement with this possibility, the CB1 antagonist SR141716A and the CB2 antagonist SR144528 prolong and enhance the pain behavior produced by tissue damage. These results indicate that peripheral CB1-like and CB2-like receptors participate in the intrinsic control of pain initiation and that locally generated anandamide and PEA may mediate this effect. (A. Calignano et al., *"Control of pain initiation by endogenous cannabinoids,"* Nature 394 (1998): 277–281).

In addition to showing that the endocannabinoids anandamide and PEA, when administered together, act synergistically and reduce pain responses 100-fold more potently than does each compound alone, the report also shows that the endocannabinoid PEA, an acylethanolamide found in the neural and non-neural tissues, inhibits mast-cell activation and reduces inflammatory responses. These results also suggest that cannabinoids can exert pain-relieving actions without having to penetrate into the central nervous system. The researchers suggest that drugs that mimic anandamide and PEA, that target CB2 receptors, or locally acting drugs that target both CB1 and CB2 receptors might be the way to avoid the psychoactive side effects and potential for abuse associated with cannabinoid receptors in the brain.

There have also been research studies that indicate that some of the other cannabinoids, flavonoids and terpenoids found in found in herbal cannabis, but not synthetic THC, may act in synergy to contribute important anti-inflammatory and other useful effects.

A 1988 study found that cannabidiol (CBD), a non-psychoactive, naturally-occurring cannabinoid found in the marijuana plant, not present in Marinol™ tablets, was more effective than aspirin in reducing inflammation. (Formukong, Evans, and Evans, *"Analgesic and Anti-inflammatory Activity of Constituents of Cannabis Sativa L"*, Inflammation, v4 1988, 361–371).

Cannabidiol (CBD) has also been shown to be a potent antioxidant as well as having potential neuroprotective and anti-inflammatory uses. Researchers found that its neuroprotective properties matched or surpassed other antioxidants in a cell culture model (A. J. Hampson et al., *"Cannabidiol and (-)delta-9-tetrahydrocannabinol are neuroprotective antioxidants"*, 95 Proceedings of the National Academy of Sciences 8268 (July 1998) and (A. M. Malfait, et al., *"The nonpsychoactive cannabis constituent cannabidiol is an oral anti-arthritic therapeutic in murine collagen-induced arthritis"*, 97 Proceedings of the National Academy of Science 9561 (August 2000).

Flavonoid components of cannabis have been shown to potentiate anti-inflammatory activity. Cannflavin A and B, common to cannabis, inhibited prostaglandin E-2 production in human rheumatoid synovial cells 30 times more potently than aspirin (Barrett, M. L., A. M. Scutt, et al., *"Cannflavin A and B, prenylated flavones from Cannabis sativa"*. Experientia 42(4): (1986) 452–453). Apigenin, a flavonoid common to cannabis and German chamomile (*Matricaria recutita* L. Asteraceae), had important anti-inflammatory actions on interleukin, TNF, carrageenan-induced edema and by inhibition of up-regulation of cytokine-induced genes (Gerritsen M E., et. al., *"Flavonoids inhibit cytokine-induced endothelial cell adhesion protein gene expression"*, Am J Pathol 147: (1995) 278–92).

Various terpenoid essential oil components of cannabis demonstrate anti-inflammatory effects at physiologically appropriate levels (McPartland, J. M., and V. Mediavilla, *"Non-cannabinoids in cannabis and cannabinoids"*, edited by F. Grotenhermen and E. B. Russo, The Haworth Press, Inc. (2001). Burstein et al., *"Prostaglandins and cannabis. III. Inhibition of biosynthesis by essential oil components of marihuana"*, Biochem Pharma-col 24(9): 1053–1054 (1975) have examined the essential oil fraction of cannabis, demonstrating eugenol as potent in prostaglandin inhibition. Alpha-pinene and caryophyllene have proven to demonstrate anti-inflammatory activity in the rat hind-paw edema model from carrageenan or by PGE-1 (Martin et al., *"Anti-inflammatory activity of the essential oil of Bupleurum fruticescens"*, Planta Med 59(6): 533–536 (1993)."

The growing body of evidence demonstrates that there are numerous synergies (the working together of two or more elements to produce an effect greater than the sum of their individual effects) between the various constituents of herbal cannabis in their interaction with the body, and that many of the constituents of cannabis do not act alone, but in concert with one another and with the cannabinoid receptors in the body to produce a range of effects.

Unlike single molecule synthetic THC, the action of the many cannabinoids, flavonoids, terpenoids, and other constituents found in herbal cannabis, and some of their metabolites, mimic the body's own endocannabinoids and interact selectively and synergistically with the presently known cannabinoid receptors CB1 and CB2 to contribute important analgesic, anti-inflammatory, and other useful effects.

The medicinal effects of cannabis cannot be defined in terms of single receptors, as it is the combination of physiological effects, induced by activation of multiple receptor types which combine to produce the overall effect. For example, relief from inflammatory pain may be predominately effected in the central nervous system (CNS) by CB1 receptors, but additional analgesic and anti-inflammatory effects are induced selectively, by CB1 and CB2 receptors in the periphery (outside the central nervous system); it is only in conjunction that a significantly greater overall benefit is achieved.

There are multiple active constituents in cannabis, including both cannabinoids and non-cannabinoids. Although these constituents may benefit the body as single elements, the significant advantage lies in their natural combination. Where there are many active components; and one element will moderate the adverse effects of another; the benefits of several elements will combine synergistically—dramatically increasing their effectiveness. For example, the endogenous cannabinoids anandamide and palmitylethanolamide have been shown to be over 100 times more effective in combination than alone. (A. Calignano et al., *"Control of pain initiation by endogenous cannabinoids,"* Nature 394 (1998): 277–281). These results are not possible with single molecule synthetic THC and THC gelatin capsules.

Another significant advantage of the multiple active constituents in herbal cannabis, is that some of the constituents modify the pharmacology of others, or cause effects of their own, and can reduce the occurrence of side effects. For example, cannabidiol (CBD), a non-psychoactive cannabinoid constituent, which has been shown to be a potent antioxidant as well as having potential neuroprotective and anti-inflammatory properties, moderates the psychotropic effects of THC.

These scientific data and studies provide evidence that the various cannabinoids extracted from the Cannabis plant and synthesized cannabinoids have a close structural relationship, and a reasonable correlation to the "endocannabinoids" or "endogenous cannabinoids" that are produced by the body of humans and animals, and that their pharmacological activity substantially parallels those compounds, both of which bind to the same cannabinoid receptors in the central nervous system (CNS) and the peripheral cannabinoid receptors in the peripheral cells and tissues outside the central nervous system.

These studies also provide an evidentiary showing of therapeutic and pharmacological utility of the present cannabinoid delivery topical liniment composition, and a reasonable correlation of the particular pharmacological activity of the cannabinoid components recited therein with endogenous cannabinoids that are known to have substantial and particular therapeutic and pharmacological utility as analgesic and anti-inflammatory agents. The present cannabinoid delivery topical liniment composition provides superior analgesic and anti-inflammatory properties that are not possible with single molecule synthetic THC and THC gelatin capsules.

There are several patents that disclose various cannabinoid compounds and compositions, some of which utilize synthetic derivations of THC and commercially available cannabinoids.

Burnstein, U.S. Pat. No. 4,847,290 discloses a non-psychoactive metabolite of THC having analgesic and anti-inflammatory properties that is in the form of an orally administered gelatin capsule. The compound utilizes a delta 1-thc-7-oic acid metabolite of THC.

Burnstein et al, U.S. Pat. No. 5,338,753 discloses a non-psychoactive derivative of THC having anti-inflammatory, analgesic and leukocyte antiadhesion properties that is in the form of an orally administered gelatin capsule, or is dissolved in vegetable oil and administered orally. The compound utilizes a (3R,4R)-delta 6-thc-7-oic acid derivative of THC.

Martin et al, U.S. Pat. No. 5,847,128 discloses a new class of water-soluble esters of tetrahydrocannabinoids, which in a preferred embodiment relates to the compound 3-(5'-cyano-1',1'-dimethylheptyl)-1-(4-N-morpholinobutyryloxy)-DELTA-8-THC, and the pharmaceutically acceptable salts of this compound. The compounds are highly soluble in aqueous solvents and medium. Pharmaceutical compositions in which the compounds are solubilized in an aqueous medium or carrier can be administered in a wide variety of delivery routes including by inhalation (e.g., via aerosol delivery) for treatment of a wide variety of conditions including pain, asthma, nausea, and the AIDS wasting syndrome. The compounds also can be used in conjunction with analgesics such as morphine in pain control treatment.

Volicer, U.S. Pat. No. 5,804,592 discloses a method of improving disturbed behavior and elevating mood in patients suffering from dementia, particularly of the Alzheimer's type, by administering dronabinol orally, buccally, sublingually, subcutaneously, intramuscularly, intravenously, transdermally, and rectally, as well as other methods of administration. Volicer does not disclose nor suggest the use of a monohydric alcohol solution.

Touitou, U.S. Pat. No. 5,540,934 discloses a liposomal composition for applying active substances to or through the skin. The composition contains vesicles in a size range up to 1743 nm, and the essential components of the composition are a phospholipid, a lower aliphatic alcohol of two to four carbon atoms (ethanol), optionally with propylene glycol, water and a compatible active ingredient. The compositions are suitable for the topical application of a wide variety of cosmetic and pharmaceutical compounds. Phospholipids are 2 fatty acids, one saturated and one unsaturated, that are linked to a glycerol (a trihydric alcohol, i.e., three —OH groups). Touitou further teaches that these compositions may also include polyols. Polyols" are "polyhydric" alcohols containing three or more hydroxyl (—OH) groups, and both "polyols" and "fatty chain" alcohols containing three or more hydroxyl (—OH) groups have virtually no ability to extract hydrophobic oils such as delta-9-THC.

None of the aforementioned studies and patents suggest the present topical cannabinoid delivery liniment analgesic and anti-inflammation formulation or treatment method for relieving pain, discomfort and tissue inflammation associated with arthritis, bursitis, fibromyalgia, carpal tunnel syndrome, gout, and other muscular and joint aches and pains.

The present invention is distinguished over the prior art in general, and these patents in particular, by a rapid-onset cannabinoid delivery topical liniment composition having analgesic and anti-inflammatory properties that contains from about 97.5% to about 99.5% by weight a 70% monohydric alcohol solution component, and from about 0.5% to about 2.5% by weight of a cannabinoid mixture extracted from the female plant *Cannabis sativa* L, selected from the group consisting of 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), terpenoids, and flavonoids. The liniment is applied topically, preferably by spraying, and the constituents of the mixture are absorbed through the skin and interact with cannabinoid receptors in the body and tissues of a mammal to produce therapeutic analgesic and anti-inflammatory effects without undesirable psychotropic side effects.

SUMMARY OF THE INVENTION

It is therefore an object of the present invention to provide a safe and effective rapid-onset cannabinoid delivery system administered topically.

It is another object of this invention to provide a rapid-onset cannabinoid delivery topical liniment having analgesic and anti-inflammatory properties.

Another object of this invention is to provide a rapid-onset cannabinoid delivery topical liniment that can be used for the relief of pain and discomfort associated with such ailments as arthritis, bursitis, fibromyalgia, carpal tunnel syndrome, gout, and other muscular and joint aches and pains.

Another object of this invention is to provide a rapid-onset cannabinoid delivery topical liniment which utilizes a combination of cannabinoids, flavonoids, terpenoids, and other constituents extracted from herbal cannabis, that mimic the body's own endocannabinoids and interact selectively and synergistically with presently known cannabinoid receptors CB1 and CB2 to contribute important analgesic, anti-inflammatory, and other useful effects.

Another object of this invention is to provide a rapid-onset cannabinoid delivery topical liniment which utilizes a combination of cannabinoids extracted from the female cannabis plant *Cannabis sativa* L that act in concert with one another and with the cannabinoid receptors in the body to produce a range of effects.

A further object of this invention is to provide a rapid-onset cannabinoid delivery topical liniment which utilizes tetrahydrocannabinol (THC) extracted from female cannabis green leaves of the plant *Cannabis sativa* L as an active ingredient, but without psychotropic effects.

A still further object of this invention is to provide a rapid-onset cannabinoid delivery topical liniment which improves circulation and provides a rejuvenating therapeutic effect.

The above noted objects and other objects of the invention are accomplished by a rapid-onset cannabinoid delivery topical liniment composition having analgesic and anti-inflammatory properties contains from about 97.5% to about 99.5% by weight a 70% monohydric alcohol solution component, and from about 0.5% to about 2.5% by weight of a cannabinoid mixture extracted from the female plant *Cannabis sativa* L, selected from the group consisting of 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), terpenoids, and flavonoids. The liniment is applied topically, preferably by spraying, and the constituents of the mixture are absorbed through the skin and interact with cannabinoid receptors in the body and tissues of a mammal to produce therapeutic analgesic and anti-inflammatory effects without undesirable psychotropic side effects.

DESCRIPTION OF PREFERRED EMBODIMENTS

The following examples describe several formulations and methods of preparation of a preferred rapid-onset cannabinoid delivery topical liniment compounded for particular use as an analgesic and anti-inflammation agent. These examples are provided for illustrative purposes only and should not be construed as limiting the scope of the invention. Many variations and applications, which do not depart from the scope and spirit of the present invention, will be apparent to those skilled in the art. All such modifications are within the intended scope of this invention.

A monohydric alcohol is used in the preparation of the present liniment composition, which facilitates extraction of the hydrophobic cannabinoids such as 9-Tetrahydrocannabinol (delta-9-THC). In a preferred embodiment, a 70% isopropyl or denatured ethyl alcohol is used. However, it should be understood that other alcohols may be used such as N-propyl alcohol and cetyl alcohol.

Preparation 1

In one formulation, the topical analgesic and anti-inflammation liniment composition is prepared by crushing from about ⅓ oz to about 1.0 oz (dry weight) of female cannabis green leaves of the plant *Cannabis sativa* L. The leaves contain hundreds of chemicals and scores of cannabinoids, including: 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), many terpenoids and several flavonoids. The concentration of the psychoactive 9-Tetrahydrocannabinol (delta-9-THC) in the plant leaves may range from about 1% to about 15% per unit of volume with a concentration of over 10% being preferred.

The crushed leaves are then placed into a mixing container. About 16 fluid oz of a 70% alcohol solution is poured into the container and mixed with the crushed leaves. The container is then tightly capped and the mixture is allowed to soak or steep in the container for about 15 to 30 days without opening the container. The container may be gently shaken every 1 to 2 days during the steeping period. After the 15 to 30 day steeping period, the mixture is strained through a strainer to remove any solids from the mixture. The solids are discarded and the liquid is poured into a dispensing container or bottle, which is then capped, and the topical liniment is ready for use.

In Preparation 1, the ratio of the dry leaves to alcohol before steeping and extraction of the cannabinoid component, may be in the range of from about 2.0% to about 7.0% by weight of the crushed leaves to from about 93% to about 98.0% by weight of the monohydric alcohol solution. After steeping and extraction, the final composition contains from about 0.5% to about 2.0% by weight of the cannabinoid component, with about 1.0% by weight of the cannabinoid component being preferred.

Preparation 2

In a second formulation, the topical analgesic and anti-inflammation liniment composition is prepared the same as Preparation 1, except that the ratio of the dry leaves to alcohol before steeping and extraction of the cannabinoid component, may be in the range of from about 3.0% to about 9.0% by weight of the crushed leaves to from about 91% to about 97.0% by weight of the monohydric alcohol solution. After steeping and extraction, the final composition contains from about 0.9% to about 2.5% by weight of the extracted cannabinoid component, with about 1.3% by weight of the cannabinoid component being preferred.

The time period for soaking or steeping the mixtures of the formulations may be shortened by heating the mixture at a temperature in the range of from about 85° F. to about 115° F. for 50 to 70 hours.

It should be understood that the cannabinoid component used in the topical analgesic and anti-inflammation liniment composition may be a mixture of various combinations selected from the group of cannabinoids, terpenoids and/or flavonoids described above such that some of the constituents modify the pharmacology of others, cause synergistic effects, or reduce the occurrence of side effects. For example, the cannabinoid component may be a mixture of the psychoactive cannabinoid delta-9-tetrehydrocannabinol (delta-9-THC) and the non-psychoactive cannabinoid Cannabidiol (CBD), wherein the delta-9-tetrehydrocannabinol (delta-9-THC) provides analgesic and anti-inflammatory effects, and the Cannabidiol (CBD) provides potent antioxidant, neuroprotective and anti-inflammatory effects, and also reduces the psychoactive effect of the delta-9-tetrahydrocannabinol (D9-THC). Cannabichromene (CBC) may be used to provide sedative and analgesic effects. Cannabigerol (CBG) may be used to provide sedative and anti-microbial effects. Terpenoids and flavonoids may be used to provide anti-inflammatory effects.

It should also be understood that the cannabinoid component used in the topical analgesic and anti-inflammation liniment composition may be a mixture of various combinations selected from the group of cannabinoids, terpenoids and/or flavonoids described above such that the constituents are selected to target and/or bypass specific cannabinoid receptors in the central and peripheral nervous system.

In a preferred method of topically applying the liniment, the liniment is sprayed onto the skin in the area of discomfort or the inflamed area. In another method of topically applying the liniment, a small amount of the liniment is applied directly to skin in the area of discomfort or the inflamed area and rubbed in by hand. The liniment may also be applied by either method over the entire body, with the exception of the face. The recommended dosage is to apply approximately 2 oz. of the liniment a day for a period of at least 1 week. The liniment may also be mixed with other liquids for various other applications.

A significant advantage of the present analgesic and anti-inflammation liniment composition is that it contains multiple active constituents and some of the constituents modify the pharmacology of others, or cause effects of their own, and can reduce the occurrence of side effects. For example, although the composition contains the psychoactive cannabinoid delta-9-tetrahydrocannabinol (D9-THC), it also contains cannabidiol (CBD), a non-psychoactive cannabinoid constituent, which has been shown to moderate the psychoactive effects of the delta-9-tetrahydrocannabinol (D9-THC) as well as being a potent antioxidant and having neuroprotective and anti-inflammatory properties. Thus, the present liniment composition, when applied as directed, does not produce undesirable psychotropic side effects.

EXAMPLES

A 78-year-old female whose joint pain required her to use a wheelchair for most of the day and to use a cane when walking was treated by spraying two oz. of the liniment of Preparation 1 over her body three times a day. After five consecutive days, she reported that joint pain and did not require a wheelchair or cane.

A 45-year-old female diagnosed as having a herniated disc and degenerative disc disease of the lower lumbar whose condition had deteriorated to having limited range of motion on the left side of her body and inability to get out of bed without assistance was treated by spraying two oz. of the liniment of Preparation 1 over her body twice a day. After two months, she reported a marked improvement in her mobility, significant reduction in pain, and was able to get out of bed without assistance.

A 61-year-old male after undergoing ultrasound of a lump under the left breast was diagnosed by a surgeon as having a bipolar rubbery concentric subareolar tissue under the breast that was compatible with Gynecomastia. The subject was treated by spraying two oz. of the liniment of Preparation 2 over the area twice a day. After nine months, the densities had resolved and have not subsequently recurred.

The above are only a few examples of a number of middle-aged persons and senior citizens who volunteered to test the present analgesic and anti-inflammation liniment compositions. In all cases, a soothing effect was reported immediately following the application of the liniment, due to the alcoholic constituent. Therapeutic effects, pain relief, and improvement in their physical condition were reported to occur from a few days to about three months of continued use on a daily basis. In cases where the liniment was sprayed over the entire body on a daily basis, the subjects reported feeling rejuvenated and having improved mobility after two to three months of treatment.

While this invention has been described fully and completely with special emphasis upon preferred embodiments, it should be understood that within the scope of the appended claims the invention may be practiced otherwise than as specifically described herein.

I claim:

1. A method of relieving a human patient of pain, discomfort and tissue inflammation associated with arthritis, bursitis, fibromyalgia, carpal tunnel syndrome, or gout, comprising the step of topically applying to the skin of the patient a liquid cannabinoid liniment composition consisting of from about 97.5% to about 99.5% by weight of 70% isopropyl alcohol solution; and from about 0.5% to about 2.5% by weight of a cannabinoid mixture extracted from the female plant *Cannabis sativa* L, in said isopropyl alcohol solution including in combination: 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), cannabinoid terpenoids, and cannabinoid flavonoids; wherein the constituents of said mixture are absorbed through the skin and interact with cannabinoid receptors in the body and tissues of the patient to produce therapeutic analgesic and anti-inflammatory effects without producing undesirable psychotropic side effects;

said Tetrehydrocannabinol (delta-9-THC) providing analgesic and anti-inflammatory effects, said Cannabidiol (CBD) providing potent antioxidant, neuroprotective and anti-inflammatory effects and reducing psychoactive effects of said Tetrahydrocannabinol (delta-9-THC), said Cannabichromene (CBC) providing sedative and analgesic effects, said Cannabigerol (CBG) providing sedative and anti-microbial effects, and said cannaboinoid terpenoids and cannabinoid flavonoids providing anti-inflammatory effects.

2. The method according to claim 1, wherein said step of topically applying comprises spraying said cannabinoid liniment composition onto the skin in the area of discomfort or inflammation.

3. The method according to claim 1, wherein said step of topically applying comprises applying a small amount of said cannabinoid liniment composition directly onto the skin in the area of discomfort or inflammation and rubbing it into the skin.

4. The method according to claim 1, wherein said step of topically applying comprises applying said cannabinoid liniment over substantially the entire body of the patient, with the exception of the facial area.

5. A rapid-onset cannabinoid delivery topical liniment composition having analgesic and anti-inflammatory properties for relieving a human patient of pain, discomfort and tissue inflammation associated with arthritis, bursitis, fibromyalgia, carpal tunnel syndrome, or gout, consisting of:
   from about 97.5% to about 99.5% by weight of 70% isopropyl alcohol solution; and
   from about 0.5% to about 2.5% by weight of a cannabinoid mixture extracted from the female plant *Cannabis sativa* L, in said isopropyl alcohol solution including in combination: 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), cannabinoid terpenoids, and cannabinoid flavonoids; wherein the constituents of said mixture are absorbed through the skin and interact with cannabinoid receptors in the body and tissues of a human patient to produce therapeutic analgesic and anti-inflammatory effects without undesirable psychotropic side effects;

said Tetrehydrocannabinol (delta-9-THC) providing analgesic and anti-inflammatory effects, said Cannabidiol (CBD) providing potent antioxidant, neuroprotective and anti-inflammatory effects and reducing psychoactive effects of said Tetrahydrocannabinol (delta-9-THC), said Cannabichromene (CBC) providing sedative and analgesic effects, said Cannabigerol (CBG) providing sedative and anti-microbial effects, and said cannaboinoid terpenoids and cannabinoid flavonoids providing anti-inflammatory effects.

* * * * *